(12) United States Patent
Holley et al.

(10) Patent No.: US 7,618,625 B2
(45) Date of Patent: Nov. 17, 2009

(54) COMPOSITIONS COMPRISING LARGE AND SMALL BINDING FRAGMENTS OF ANTIBODIES AGAINST THE SAME TOXIN

(75) Inventors: Jane Louise Holley, Salisbury (GB); Carl Nicholas Mayers, Salisbury (GB); David Whitfield, Salisbury (GB); Timothy John Gilby Brooks, Salisbury (GB)

(73) Assignee: The Sectetary of State for Defence, Salisbury, Wiltshire (GB)

( * ) Notice: Subject to any disclaimer, the term of this patent is extended or adjusted under 35 U.S.C. 154(b) by 0 days.

(21) Appl. No.: 10/559,148

(22) PCT Filed: Jun. 3, 2004

(86) PCT No.: PCT/GB2004/002351
§ 371 (c)(1),
(2), (4) Date: Aug. 17, 2006

(87) PCT Pub. No.: WO2004/106376
PCT Pub. Date: Dec. 9, 2004

(65) Prior Publication Data
US 2007/0036805 A1 Feb. 15, 2007

(30) Foreign Application Priority Data
Jun. 3, 2003 (GB) .................................. 0312642

(51) Int. Cl.
*A61K 39/00* (2006.01)
*A61K 39/395* (2006.01)
*A61K 39/40* (2006.01)

(52) U.S. Cl. .............. 424/130.1; 424/135.1; 424/141.1; 424/150.1

(58) Field of Classification Search ............... 424/130.1
See application file for complete search history.

(56) References Cited

U.S. PATENT DOCUMENTS
2005/0042775 A1* 2/2005 Pomato et al. .............. 436/547

OTHER PUBLICATIONS

Stockwin et al, The role of therapeutic antibodies in drug discovery, 2003, Biochem Soc Trans, vol. 31, p. 433-436.*

Habermann et al (Med. Microbiol. Immunol. Vol. 161, pp. 203-210, 1975).*

Behr, at at, 'Anti-Carcinoembryonic antigen Antibodies versus Somatostatin Analogs in the Detection of Metastatic Medullary Thyroid Carcinoma.' *Sixth Conference on Radioimmunodetection and Radioimmunotherapy of Cancer*, Supplement to Cancer, pp. 2436-2457(1997).

Hibbs, et al., 'Experience with the Use of an Investigational F(ab')$_2$ Heptavalent Botulism Immune Globulin of Equine Origin During an Outbreak an Outbreak of Type E Botulism in Egypt,' *Clinical Infectious Diseases*, 23:337-340 (1996).

Ismail, et al., 'Pharmacokinetics of $^{125}$ I-Labelled IgG, F(ab')$_2$and Fab Fractions of Scorpion and Snak Antivenins: Merits and Potential for Therapeutic Use.' *Toxicon*, 36(11):1523-1528 (1998).

Mayers, etal., 'Anti-immunoglobulin Responses to IgG,F(ab')$_2$ and Fab Botulinum Antitoxins in Mice,' *Immunopharmacology and Immunotoxicology*, 25(3):397-408 (2003).

Mayers, et al., 'Antitoxin therapy for botulinum Intoxication,' *Reviews in MedicalMicrobiology*, 12(1):29-37 (2001).

Muller, et al., 'Phage-displayed and soluble mouse scFv fragments neutralize rabies virus,' *Journal of Virological Methods*, 87:221.233(1997).

Steele, etal., 'Further Evidence for Cross-Linking as a Protective Factor in Experimental Cholera: Properties of Antibody Fragments,' *The Journal of Infectious Diseases*,132(2):175-180 (1975).

Vassilev, at al., 'Protective Activity of Two Human Intravenous immunoglobulin Preparations in Experimental Infection with an Encapsulated Staphylococcus Aureus Strain,' *Acta Microblologica Hungarica*, 34(2):139-145 (1987).

Vaz, et al., 'Higher protective activity of Fab fragment compared to F(ab')2 and IgG on experimental tetanus,' *Mircen Journal of Appl. Microbial. & Biotech.*, 4(3):339-348 (1988).

* cited by examiner

*Primary Examiner*—Mark Navarro
(74) *Attorney, Agent, or Firm*—Kilpatrick Stockton LLP

(57) ABSTRACT

A pharmaceutical composition comprising (i) a first specific binding agent selected from an antibody or a large binding fragment of an antibody which specifically binds a target toxin, and (ii) a second specific binding agent which comprises a small binding fragment of an antibody which binds said toxin. The compositions are used in the treatment of toxin poisoning, for example following exposure to toxins such as Botulinum toxins.

14 Claims, 3 Drawing Sheets

COMPOSITIONS COMPRISING LARGE AND SMALL BINDING FRAGMENTS OF ANTIBODIES AGAINST THE SAME TOXIN

CROSS REFERENCE TO RELATED APPLICATIONS

This application is the U.S. national phase of International Application No. PCT/GB2004/002351 filed Jun. 3, 2004 published in English on Dec. 9, 2004 as International Publication No. WO 2004/106376 A1, which application claims priority to Great Britain Application No. 0312642.2 filed Jun. 3, 2003, the contents of which are incorporated by reference herein.

The present invention relates to pharmaceutical compositions containing combinations of antibody fragments, useful in the treatment of various conditions and in particular in the treatment of conditions caused by toxins. Methods of treatment utilising these compositions form a further aspect of the invention.

The concept of using animal or human-derived polyclonal antibodies and antidotes or antisera against toxins is well established. The British Pharmacopoeia lists antisera against a number of venoms and toxins produced by micro-organisms, as well as poisonous animals such as snakes and scorpions.

The antisera are obtained by fractionation of the serum of horses or other mammals that have been immunised against the toxin of interest. In general, the active component of the antiserum consists of whole antibodies (e.g. IgG, IgT) although in recent years, there has been a move towards the use of despeciated antibody fragments such as $F(ab)_2$ and $F(ab')_2$.

These fragments have the advantage of producing fewer side effects in the patients, and thus an improvement in safety.

When dealing with the victims of some toxin intoxication however, there is a very short window of opportunity during which any medical countermeasures are effective.

The present invention provides a pharmaceutical composition comprising (i) a first specific binding agent selected from an antibody or a large binding fragment of an antibody which specifically binds a target toxin, and (ii) a second specific binding agent which comprises a small binding fragment of an antibody which binds said toxin.

Compositions of the invention have been found provide rapid and sustained antitoxin activity. This may be due to the fact that the compositions are able to produce an effect, which utilises the mutually complementary properties of the first and second specific binding agents to provide sustained antitoxin capability.

One factor that affects the window of opportunity in the treatment of toxin intoxication is the speed with which the antitoxin is distributed around the body to the sites of action of the toxin. Molecules of the first specific binding agent appear to be less extensively distributed into the extravascular space than molecules of the second specific binding agent. The second specific binding agent appears to provide an antitoxin capability that penetrates rapidly into the extravascular space to provide rapid protection.

The binding of antibodies such as IgG and fragments to toxins is reversible, and therefore there is a risk of a "rebound" effect due to toxin being released, unless at least some functional antibody or antibody fragment remains in the plasma to bind any released toxin. Rapid clearance of the smaller molecules of the second specific binding agent may mean that they are less available in the plasma to "mop up" released toxin. However, by virtue of their slower clearance and higher residual plasma level, the first specific binding agent may bind any toxin released and thereby minimise the rebound effect. In addition, they provide prolonged protection by virtue of their lower clearance rate.

The first and second binding agents may bind the same or different antigens provided they are associated with the same toxin.

Suitably they have an inactivating effect on the toxin, and prevent the toxin from entering cells.

As used herein, the term "toxin" includes poisons and venoms produced by living organisms, such as bacteria, plants, snakes or insects such as scorpions. It may also include synthetic poisons.

The first specific binding agent may comprise an antibody such as an immunoglobulin, which may be IgG, IgM, IgE, IgA, IgD or any subclass thereof, but in particular is an IgG or IgT. The dosages of first specific binding agent required in a composition of the invention is lower than would be required conventionally and therefore adverse side effects or reactions, such as the possibility of anaphylactic shock, may be reduced or minimised. However, if desired the antibody may be "humanised" using conventional methods, or comprise a chimeric antibody.

In particular however, the first specific binding agent comprises a large binding fragment of an antibody.

As used herein the expression "large binding fragment" refers to an antibody fragment that comprises a significant proportion of the antibody from which it is derived. For instance, it will comprise the entire variable domain, as well as some of a constant region (Fc). In particular, large antibody fragments include $F(ab')_2$ or $F(ab)_2$ fragments, but they may also comprise deletion mutants of an antibody sequence.

In particular the first specific binding agent comprises a large binding fragment selected from $F(ab')_2$ or $F(ab)_2$ fragments. The acronyms used here are conventional in the art and are understood by a skilled person.

The expression "small binding fragment" refers to an antibody fragment which lacks a significant element of the antibody from which it is derived, for instance, it may lack a significant proportion of the $F_c$ chain, provided it retains it ability to bind the toxin. In particular, small antigen binding fragments include Fab or Fab' fragments, as well as single chain (sc) antibodies, FV, VH or VK fragments.

In particular the second specific binding agent comprises a small binding fragment selected from Fab or Fab' fragments.

Preferably at least one of the first or second specific binding agents will include a section corresponding to part of the Fc region of the antibody.

Antibodies used in the compositions of the invention, or from which the large and small binding fragments are derived may be polyclonal or monoclonal, which may be produced using conventional methods.

For instance, polyclonal antibodies may be generated by immunisation of an animal (such as a rabbit, rat, goat, horse, sheep etc) with the toxin or immunogenic subunits or fragments thereof, to raise antisera, from which antibodies may be purified.

Monoclonal antibodies may be obtained by fusing spleen cells from an immunised animal such as with hybridoma cells, and selecting cells which secrete suitable antibodies.

Antibody binding fragments for use in the compositions, whether large or small, are suitably derived from polyclonal or monoclonal antibodies using conventional methods such as enzymatic digestion with enzymes such as papain or pepsin (to produce Fab and $F(ab')_2$ fragments respectively). Alternatively, they may be generated using conventional recombinant DNA technology.

Small and large antigen binding fragments used in the composition of the invention may be derived from the same or different sets or source of antibody. They may be specific for the same or different antigens, provided that the antigens are associated with the same toxin.

In particular the antigen is associated with a toxin which is required to be inactivated in a patient. The toxin may be present as a result of exposure to the toxin. For example toxins such as botulinum toxin, anthrax toxin or plant derived toxins such as ricin toxin, may be inhaled in biological warfare situations or in laboratory accidents, or they may be ingested in food containing them. The latter also applies to *Staphylococcal* enterotoxins, which are typically associated with food poisoning. Alternatively, toxins may be produced as a result of infection with an organism. Particular organisms known to produce toxins include *C. botulinum*, such as is found in wound botulism or infant botulism, clostridial species in general, for example *C. perfringens, C. bifermentans, C. difficile* or *C. tetani, Staphylococcus* species and *Bacillus anthracis* which produces anthrax toxins.

In particular, the antigen is associated with a botulinum toxin, which may be any of type A, B, C, D, E, F of G.

Compositions of the invention may comprise first and second specific binding agents, which bind more than one toxin molecule, for example, a range of toxins produced by the same microorganism or animal. Thus the specific binding agents may be multivalent in nature, or they may be specific for antigens which are common to more than one toxin. Alternatively, the compositions may comprise more that one "set" of first and second specific binding agents, each set being specific for a different toxin molecule.

In a particular embodiment, the composition of the invention comprises two "sets" of first and second specific binding agents, each set binding a different botulinum toxin A, B, C, D, E or F. Preferably at least three sets of first and second specific binding agents are present, and most preferably, sets of specific binding agents which are specific for all of toxins A-F are included.

Suitably, in each case, the ratio of the first specific binding agent to the second specific binding agent is in the w/w ratio of 90:10 to 10:90, more suitably from 70:30 to 30:70 or and preferably from 60:40 to 40:60.

Compositions of the invention may further comprise pharmaceutically acceptable carriers or excipients as are well known in the art. They may be solid or liquid carriers depending upon the intended mode of administration.

Any desired mode of administration may be used, and this will depend upon factors such as the nature of the toxin being treated, and the nature of the patient. In particular compositions of the invention will be intended for oral, parenteral (especially intravenous) or intranasal administration, or for administration by inhalation or insufflation.

Oral compositions may be in the form of tablets, lozenges, hard or soft capsules, aqueous or oily suspensions, emulsions, dispersible powders or granules, syrups or elixirs. Compositions for parenteral administration will suitably be in the form of a sterile aqueous or oily solution for intravenous, subcutaneous, or intramuscular dosing.

Compositions for intranasal administration or for administration by inhalation or insufflation will suitably comprise a finely divided powder, and inhalable compositions may also be in the form of a liquid aerosol.

Compositions of the invention may comprise other components such as preservative agents, inert diluents, granulating and disintegrating agents, binding agents, lubricating agents, anti-oxidants as well as colouring, sweetening or flavouring agents, depending upon the nature of the composition.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

The relative amounts of pharmaceutically acceptable carrier to the first and second binding agents in a formulation will vary depending upon factors such as the particular route of administration. Generally however, compositions will comprise from about 1 to about 98 percent by weight of pharmaceutically acceptable carrier, and preferably from 5 to 90 percent by weight of pharmaceutically acceptable carrier.

The size of the dose for therapeutic purposes of a composition of the invention will naturally vary according to the nature and severity of the condition, the age and sex of the animal or patient and the route of administration, according to well known principles of medicine. Generally however, patients are given from 0.5 mg to 75 mg per kg body weight of the first and second binding agents.

Compositions of the invention are suitably administered to a patient in need thereof, as soon as possible after exposure to the toxin. In the case of a poisoning incident, such as a snake or scorpion bite, this may be carried out as soon as possible after the incident has occurred. In the case of toxins produced by microorganisms, which have infected a patient and where exposure is not known of, the compositions are suitably administered as soon as symptoms are noted.

Early administration of the composition of the invention is particularly effective, as the inclusion of the second binding agent results in fast inactivation of toxin molecules, which may prevent the toxin entering cells, to cause irreparable damage. The window of opportunity will vary depending upon the particular patient or animal exposed, and the dosage of the toxin.

In a further aspect, the invention provides a combination of (i) a first specific binding agent selected from an antibody or a large binding fragment of an antibody which specifically binds a target toxin, and (ii) a second specific binding agent which comprises a small-binding fragment of an antibody which binds said toxin, for use in the treatment of the effects of the toxin.

Thus in yet a further aspect, the invention provides the use of a combination of (i) a first specific binding agent selected from an antibody or a large binding fragment of an antibody which specifically binds a target toxin, and (ii) a second specific binding agent which comprises a small binding fragment of an antibody which binds said toxin, in the preparation of a medicament for the treatment of the effects of the toxin.

The invention further comprises a method of preventing the effects of a toxin on a mammal such as a human, said method comprising administering to a mammal in need thereof, a composition as described above.

The composition is suitably administered as soon as possible after the toxin has entered the mammal's body, either as a result of a poisoning incident or as a result of infection with a microorganism, which produces a toxin. Repeat administrations using the administration methods and dosages in accordance with standard clinical practice, may be necessary.

The invention will now be particularly described by way of example with reference to the accompanying diagrammatic drawings in which.

EXAMPLE 1

Studies were carried out to investigate the effectiveness of goat derived polyclonal antisera raised against toxoids of botulinum toxin (types A to E). The antisera was purified to whole IgG and its fragments F(ab')$_2$, Fab' and Fab using conventional methods.

Balb/c mice (6 per group) were given type A botulinum toxin (100MLD$_{50}$) intraperitoneally. Thirty minutes laters, antitoxin treatment consisting of antibodies, or fragments or combinations were administered intravenously. Treatment groups consisted of:
1. IgG (2 mg)
2. F(ab')$_2$ (1.6 mg)
3 IgG (1 mg)+Fab(0.8 mg)
4. IgG (1 mg)+F(ab')$_2$(0.8 mg)
5. F(ab')$_2$(0.8 mg)+F(ab)(0.8 mg)
6. F(ab')$_2$(0.8 mg)+F(ab')(0.8 mg)
7. F(ab') (1.6 mg)
8. Fab (1.6 mg)

Thus, when given as combinations, the doses of each were reduced to maintain equimolar doses of antigen recognition sites. The ability of the individual fragments and combinations to protect mice from death and also to reduce symptoms of intoxication was monitored. Symptom scores were calculated as follows:
1=increased rate of breathing
2=1+slight pinching of abdomen
3=1+medium pinching of abdomen
4=1+medium pinching of abdoment+pilo erection.

Figure 1:
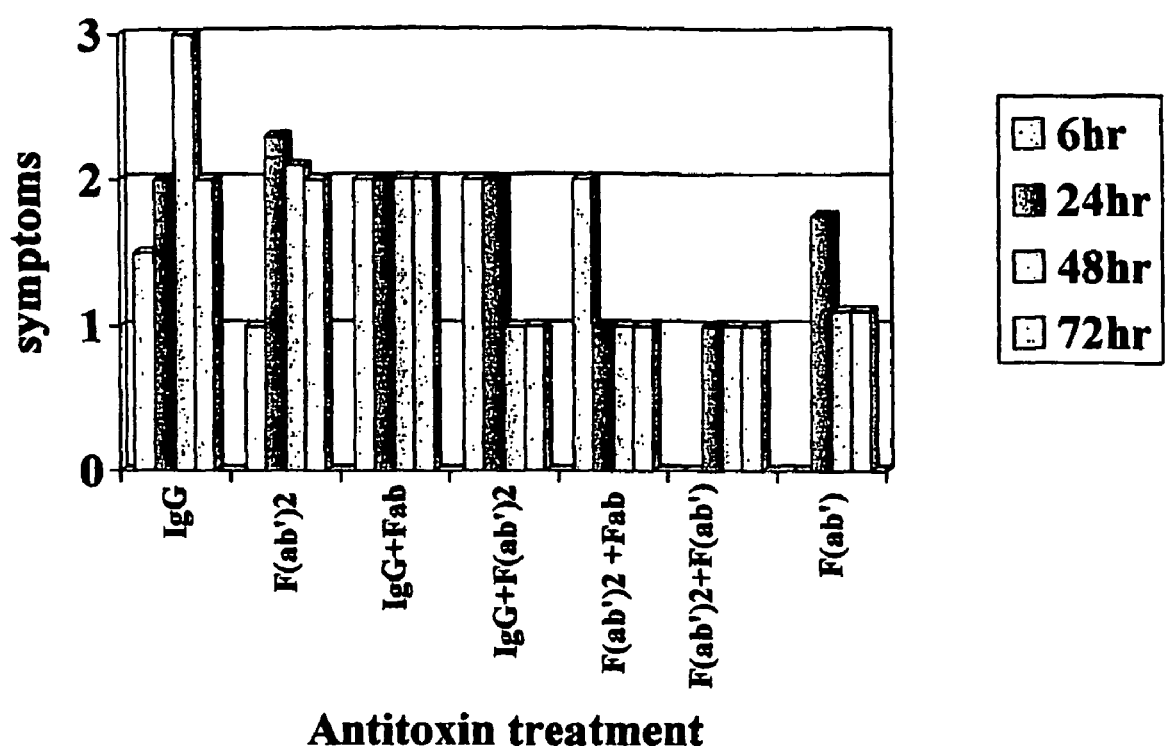
FIG. 1 shows a summary of the results of a range of therapies including those of the invention on the symptoms observed in mice to which the therapies were administered 30 minutes after exposure to Type A botulinum toxin (100MLD$_{50}$)

The symptom scores (mean per group) at various times measured at 6, 24, 48 and 72 hours after administration are shown in FIG. 1. The Fab fragment alone was unable to prevent death.

It was found that, when administered as individual fragments, IgG, F(ab')$_2$ and Fab' were equally effective at preventing death. However, the combinations of fragments gave better protection against the development of symptoms.

The graph of FIG. 1 shows that the combination of F(ab')$_2$ with either Fab or F(ab') gave a reduction in the severity of symptoms observed at various time points during the next few days compared to other combinations or fragments alone. All animals went on to fully recover.

EXAMPLE 2

Variation in Composition of the Combination

Figure 2:
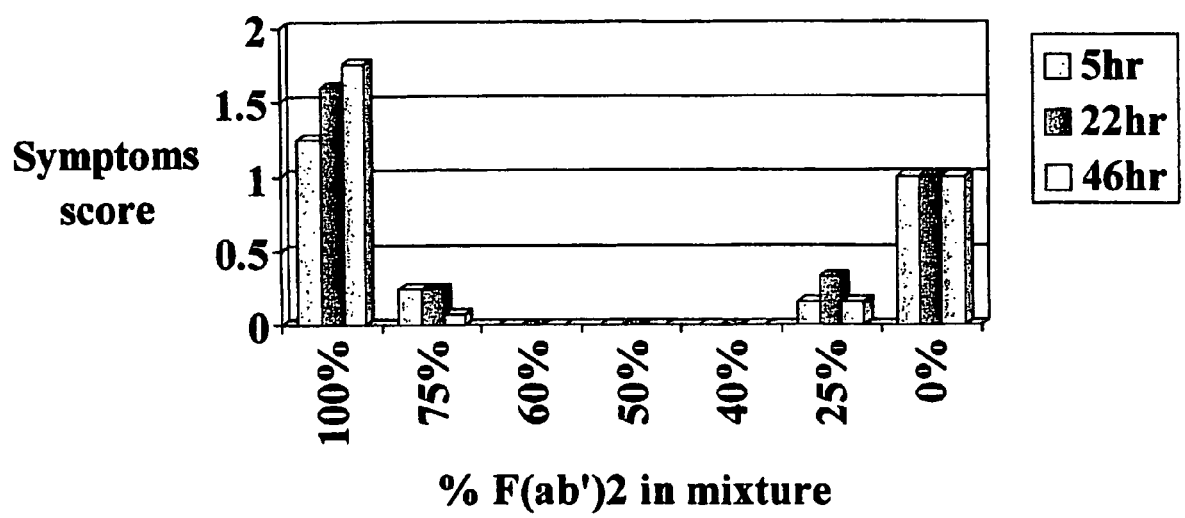
FIG. 2 illustrates the mean symptoms score produced following administration of compositions comprising varying amounts of the components of the compositions of the invention to mice 20 minutes after exposure to Type A botulinum toxin (100MLD$_{50}$)

In order to determine the effect of altering the ratio of F(ab')$_2$ and Fab' on prevention of development of symptoms of intoxication in mice following toxin administration, F(ab')$_2$ and Fab' were administered intravenously in varying proportions, with a total dose always of 1.6 mg, 20 minutes after intraperitoneal administration of 100MLD$_{50}$ of type A botulinum toxin. Again symptoms were recorded at various times using the symptom scoring route
1=increased rate of breathing
2=1+slight pinching of abdomen The group means are shown in FIG. 2.

It is clear that the combinations were all better than the individual fragments alone. Furthermore, complete prevention of symptoms was possible using a combination of F(ab')$_2$ and Fab' administered within the early window of opportunity (i.e. within 20 minutes of exposure), and prevent any symptoms developing compared to mild symptoms developing with the fragments when used alone. This was achieved using relative proportions of the fragments in the range of from a 6:4 mixture to a 4:6 mixture.

EXAMPLE 3

Investigation of the Therapeutic Window

Although it was found that the combination of the invention did not generally lengthen the therapeutic window (results not shown), if administered early, the combination of the invention did lead to a reduction in symptoms.

Figure 3:
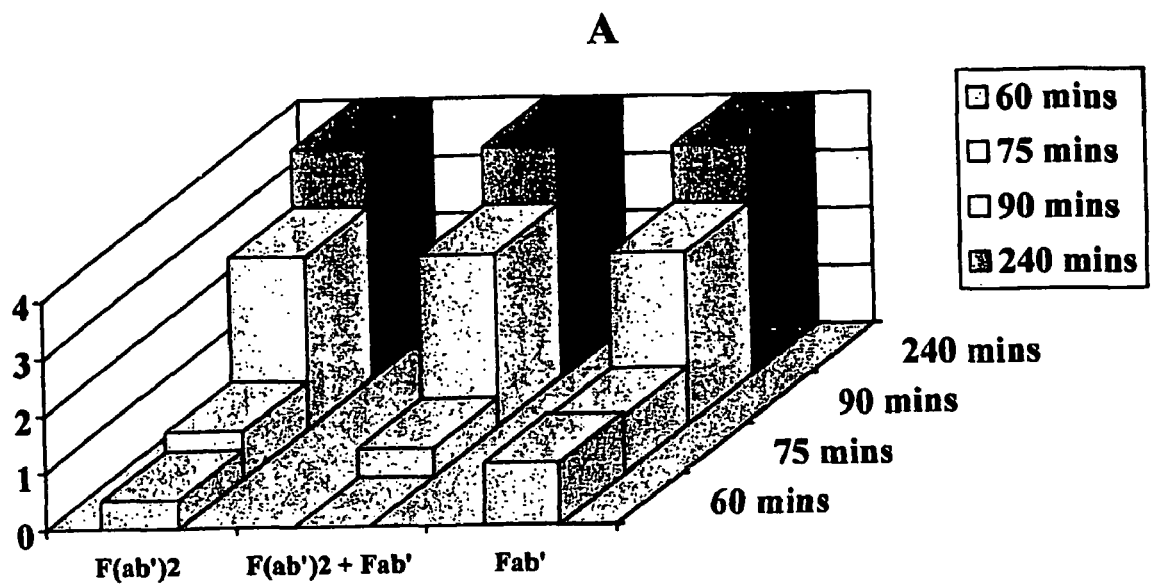
FIG. 3 shows a comparison of symptoms of botulinum intoxication in surviving mice following post-exposure therapy with individual antitoxin fragments or combinations.
Figure 3:
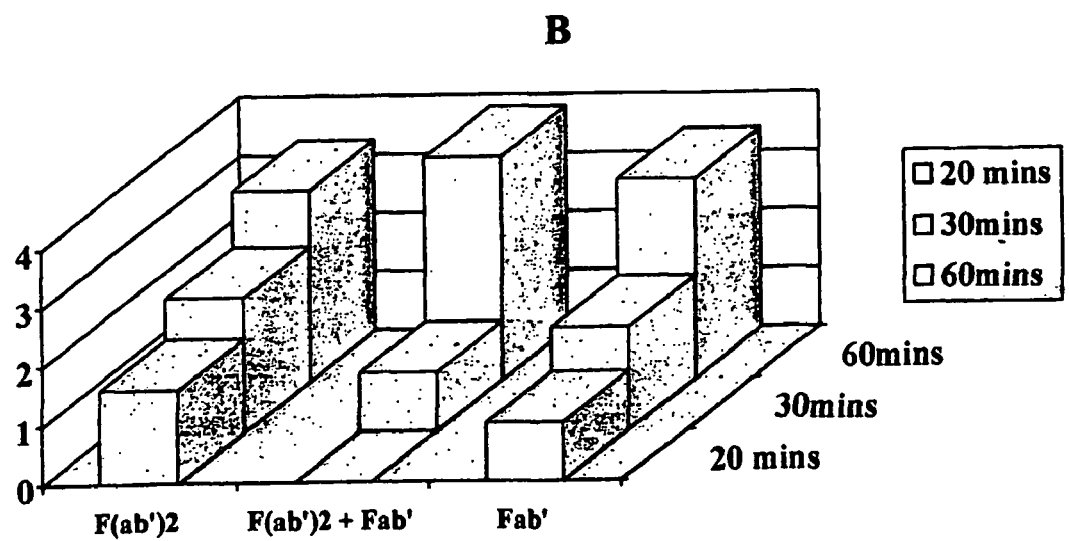

Groups of six balb/c mice were dosed intravenously with one of the following treatment regimes:
1. F(ab')$_2$ (1.6 mg)
2. F(ab')$_2$ (0.8 mg)+Fab' (0.8 mg)
3. Fab' (1.6 mg)

at various time points (60, 75, 90 or 240 minutes) following ip administration of 10 MLD$_{50}$ type A botulinum toxin. Symptoms of individual mice were scored 24 hours later using the scoring scale described in Example 1 above. The mean score per group per time point are shown in FIG. 3A.

The experiment was repeated, but on this occasion, the mice were given 100MLD$_{50}$ type A botulinum toxin and the antitoxins were given at either 20, 30 or 60 minutes later. Symptoms of individual mice were scored 24 hours later using the scoring scale described in Example 1 above. The mean score per group per time point are shown in FIG. 3B.

These results suggest that beyond a certain time point following exposure enough toxin has entered the cells to cause irreparable damage and no therapy can be successfully reverse these effects. If given early enough, the fragments can prevent the emergence of any symptoms of intoxication, but the effect of the combination is better.

However at interim time points, symptoms of intoxication are apparent although the animals usually recover fully. At early and interim time points, the use of a combination of antitoxin fragments produced clear superiority in the reduction of the severity of symptoms that develop in comparison to the fragments or IgG administered alone. This is an important finding as the milder the symptoms the less incapacitating the illness is.

The invention claimed is:

1. A pharmaceutical composition comprising (i) a first specific binding agent, which is an F(ab')$_2$ or F(ab)$_2$ antibody fragment that specifically binds a target toxin, and (ii) a second specific binding agent that comprises a small binding antibody fragment that binds the target toxin, wherein the small binding fragment is selected from the group consisting of Fab, Fab', a single chain (sc) antibody, or FV, VH, or VK fragments.

2. The composition of claim 1 wherein the second specific binding agent is an Fab or Fab' fragment.

3. The composition of claim 1 wherein the first and/or second binding agents are from polyclonal antibodies.

4. The composition of claim 1 wherein the first and/or second binding agents are from monoclonal antibodies.

5. The composition of claim 1 wherein the toxin is a Botulinum toxin.

6. The composition of claim 5 wherein the first and second specific binding agents bind at least one of type A, B, C, D, E, F or G botulinum toxin.

7. The composition of claim 6 wherein the composition comprises sets of first and second specific binding agents each set of specific binding agents binding a different one of botulinum toxins A, B, C, D, E, F or G.

8. The composition of claim 1 wherein the w/w ratio of the first specific binding agent to the second specific binding agent is in the range of from 90:10 to 10:90.

9. The composition of claim 8 wherein the w/w ratio of the first specific binding agent to the second specific binding agent is in the range of from 70:30 to 30:70.

10. The composition of claim 9 wherein the w/w ratio of the first specific binding agent to the second specific binding agent is in the range of from 60:40 to 40:60.

11. The composition of claim 1 which further comprises a pharmaceutically acceptable carrier or excipient.

12. The composition of claim 1 which is suitable for oral, parenteral, or intranasal administration, or for administration by inhalation or insufflation.

13. A pharmaceutical composition comprising (i) an antibody that specifically binds a Botulinum toxin and (ii) a small binding fragment of an antibody that specifically binds a Botulinum toxin selected from the group consisting of Fab, Fab', a single chain (sc) antibody, FV, VH, and VK fragments.

14. The pharmaceutical composition of claim 13 wherein the antibody is IgG or IgT.

\* \* \* \* \*